(12) United States Patent
Low et al.

(10) Patent No.: US 11,446,297 B2
(45) Date of Patent: Sep. 20, 2022

(54) METHODS FOR TREATING HEMOLYTIC DISEASES AND SICKLE CELL DISEASE

(71) Applicants: Purdue Research, West Lafayette, IN (US); Francesco Turrini, Sassari (IT); Antonella Pantaleo, Sassari (IT)

(72) Inventors: Phillip S. Low, West Lafayette, IN (US); Francesco Turrini, Sassari (IT); Antonella Pantaleo, Sassari (IT)

(73) Assignees: Purdue Research Foundation, West Lafayette, IN (US); Francesco Turrini, Sassari (IT); Antonella Pantaleo, Sassari (IT)

( * ) Notice: Subject to any disclaimer, the term of this patent is extended or adjusted under 35 U.S.C. 154(b) by 24 days.

(21) Appl. No.: 15/566,590

(22) PCT Filed: Apr. 14, 2016

(86) PCT No.: PCT/US2016/027501
§ 371 (c)(1),
(2) Date: Oct. 13, 2017

(87) PCT Pub. No.: WO2016/168444
PCT Pub. Date: Oct. 20, 2016

(65) Prior Publication Data
US 2018/0078552 A1    Mar. 22, 2018

Related U.S. Application Data (60) Provisional application No. 62/147,220, filed on Apr. 14, 2015.

(51) Int. Cl.
*A61K 31/505* (2006.01)
*A61K 31/506* (2006.01)

(52) U.S. Cl.
CPC .......... *A61K 31/506* (2013.01); *A61K 31/505* (2013.01)

(58) Field of Classification Search
CPC ............................ A61K 31/506; A61K 31/505
See application file for complete search history.

(56) References Cited

U.S. PATENT DOCUMENTS

| | | | |
|---|---|---|---|
| 8,057,815 B2 | 11/2011 | Andre et al. | |
| 2005/0232969 A1* | 10/2005 | Andre ................. | A61K 31/473 424/423 |
| 2014/0309233 A1 | 10/2014 | Low et al. | |
| 2015/0158925 A1* | 6/2015 | Waller ................... | A61K 35/28 424/158.1 |
| 2017/0189357 A1* | 7/2017 | Zennadi ............... | G01N 33/573 |

OTHER PUBLICATIONS

Genovese et al 'An Oral Syk Kinase Inhibitor in the Treatment of Rheumatoid Arthritis' Arthritis and Rheumatism, 63(2), p. 337-345, 2011.*
Rubin et al., Red Blood Cell Microparticles: Clinical Relevance, Transfusion Medicine and Hemotherapy, Aug. 27, 2012.*
Falanga et al., "Circulating microparticles in children with sickle cell anemia: a heterogeneous procoagulant storm directed by hemolysis and fetal hemoglobin," haematologica 2013; 98(7).*
Terra et al., "Increased Tyrosine Phosphorylation of Band 3 in Hemoglobinopathies," American Journal of Hematology 58:224-230 (1998).*
Ferru et al., "Regulation of membrane-cytoskeletal interactions by tyrosine phosphorylation of erythrocyte band 3," Blood. 2011;117(22):5998-6006.*
International Search Report and Written Opinion issued by the ISA/US, Commissioner for Patents, dated Aug. 11, 2016, for International Application No. PCT/US2016/027501; 9 pages.
Kutlar, A., "GLEE-ful for sickle cell pain?" Blood, Sep. 12, 2013, vol. 122, No. 11, pp. 1846-1847.
Stojanovic, K.S., et al., "Chronic myeloid leukaemia and sickle cell disease: could imatinib prevent vaso-occlusive crisis", 2011 Blackwell Publishing Ltd., British Journal of Haematology, vol. 155, pp. 271-272.
Murphy, M., et al., "Effectiveness of Imatinib Therapy for Sickle Cell Anemia and Chronic Myeloid Leukemia," The American Journal of the Medical Sciences, vol. 347, No. 3, Mar. 2014, pp. 254-255.
International Preliminary Report on Patentability received for PCT Patent Application No. PCT/US16/27501, dated Oct. 26, 2017, 7 pages.

* cited by examiner

*Primary Examiner* — Jared Barsky
(74) *Attorney, Agent, or Firm* — Schwegman Lundberg & Woessner, P.A.

(57) ABSTRACT

The present disclosure generally relates to methods of treating hemolytic diseases such as sickle cell anemia using kinase inhibitors, for example, compounds that inhibit the spleen tyrosine kinase (SYK). In some embodiments a method is presented to prevent thrombosis in blood vessels of patients with a hemolytic disease comprising the step of: administrating to a patient having at least one hemolytic disease a therapeutically effective amount of at least one SYK inhibitor. In some embodiments the method includes repeatedly administering the SYK kinase inhibitor to a patient.

7 Claims, 2 Drawing Sheets

METHODS FOR TREATING HEMOLYTIC DISEASES AND SICKLE CELL DISEASE

PRIORITY CLAIM

This application is a U.S. National Stage Application of International Patent Application No. PCT/2016/027501, filed Apr. 14, 2016, which claims the benefit of U.S. Provisional Patent Application No. 62/147,220 filed on Apr. 14, 2015, the entire disclosures of both of which are hereby expressly incorporated by reference herein.

TECHNICAL FIELD

The present disclosure generally relates to methods of treating hemolytic diseases using SYK inhibitors.

BACKGROUND AND SUMMARY

This section introduces aspects that may help facilitate a better understanding of the disclosure. Accordingly, these statements are to be read in this light and are not to be understood as admissions about what is or is not prior art.

Patients who are afflicted with sickle cell disease (SCD) can suffer greatly from recurring episodes of sickle cell crisis: the extreme pain associated with the obstruction of one or more blood vessels and the inflammation resulting from this blockage. The pain of such a vaso-occlusive crisis (VOC) has been described as severe and life-limiting. Cessation of blood flow will eventually cause severe organ damage. However, it is the pain episodes and fear of their recurrence which degrades the quality of life for those affected by this disease.

Immediate treatment of VOC involves hospitalization and administration of opioid analgesics. Ongoing care involves episodic use of analgesics and chronic dosing of hydroxyurea (HU), an agent that enhances expression of fetal hemoglobin and is a known suppressor of the sickling process. A placebo-controlled, double-blind, prospective trial in severely affected adults with Hb SS (a type of sickle cell disease) showed that HU significantly reduced the recurrence of vaso-occlusive pain and acute chest syndrome. A multi-center phase I/II trial in children >5 years-of-age showed safety and hematologic effects similar to those observed in adults. Yet these treatments also have their problems. Frequent opioid use induces drug tolerance, increased dosing and problems with dependence which further increase the burden on these patients. HU is a potentially toxic chemotherapeutic agent whose long-term toxicity (including concerns about carcinogenicity and teratogenicity) is unresolved. Thus the drug should be initiated and monitored only by hematologists with expertise in chemotherapy and sickle cell disease and after written documentation of patient education and consent. The drug is FDA-approved only for selected adult patients, with the important caution that the drug is not curative and requires close hematologic monitoring for myelotoxicity and the strict use of contraception by both men and women who are sexually active. While there is a need in the art for an alternative prophylactic treatment to prevent the onset of intense pain associated with a vaso-occlusive crisis, there is an even greater need for a treatment which improves the quality of life for sickle cell patients by relieving the chronic pain that must now be masked by analgesics.

A aspects of disclosure provides details on a new method of alleviating the chronic pain of sickle cell disease and preventing vaso-occlusive crises comprising the administration to a patient in need thereof a therapeutically effective amount of a tyrosine kinase inhibitor. In some embodiments the method includes repeatedly administering the tyrosine kinase inhibitor. In some embodiments the method includes a spleen tyrosine kinase (SYK) inhibitor. In one aspect, the disclosure provides a method of interfering with the phosphorylation of tyrosine residues 8 and 21 on the erythrocyte membrane protein known as Band 3. In other aspects, the method includes imatinib mesylate, one or more analogs of imatinib, or different salts or other forms of imatinib. In other aspects, the tyrosine kinase inhibitor is imatinib mesylate (GLEEVEC).

In other aspects, a method is presented to interfere with the phosphorylation of a protein Band 3 comprising introduction of a spleen tyrosine kinase inhibitor to an erythrocyte. In some embodiments, the method includes introducing a kinase inhibitor through the membrane and into the cytoplasm of the erythrocyte. In other aspects, the method includes imatinib mesylate, one or more analogs of imatinib, or different salts or other forms of imatinib. In other aspects, the tyrosine kinase inhibitor is GLEEVEC.

A first embodiment of the present disclosure includes a method of treating vaso-occlusive crises, comprising the steps of: administering to a patient in need thereof a therapeutically effective dose of a tyrosine kinase inhibitor.

A second embodiment of the present disclosure includes the first embodiment, wherein the therapeutically effective dose of the tyrosine kinase inhibitor is in the ranges selected from the group consisting of: about 100 mg/day to about 2000 mg/day, about 100 to about 2000 mg/day, about 100 to about 1800 mg/day, about 100 to about 1600 mg/day, about 100 to about 1400 mg/day, about 100 to about 1200 mg/day, about 100 to about 1000 mg/day, about 100 to about 800 mg/day, about 100 to about 600 mg/day, about 100 to about 400 mg/day, from about 100 to about 200 mg/day, and wherein the dose of the tyrosine kinase inhibitor is administered to the patient at least once per day.

A third embodiment of the present disclosure includes any one of the first and second embodiments, wherein the therapeutically effective dose of the tyrosine kinase inhibitor is on the order of between about 200 mg/day and about 500 mg/day and the dose of the tyrosine kinase inhibitor is administered to the patient at least once per day.

A fourth embodiment of the present disclosure includes any one of the first to the third embodiments, wherein the tyrosine kinase inhibitor is a spleen tyrosine kinase inhibitor.

A fifth embodiment of the present disclosure includes any one of the first to the fourth embodiments, wherein the spleen tyrosine kinase inhibitor is at least one inhibitor selected from the group consisting of: spleen tyrosine kinase inhibitor II, spleen tyrosine kinase inhibitor IV, imatinib, imatinib mesylate, NVP-QAB205, purine-2-benzamine derivatives, 1,6-naphthyridine derivatives, BAY 61-3606, piceatannol, 3,4-dimethyl-10-(3-aminopropyl)-9-acridone oxalate), 3,4-dimethyl-10-(3-aminopropyl)-9-acridone oxalate, substituted azaindoles, Fostamatinib disodium, tamatinib, oxindoles, 3,3'-[(5-Fluoro-2,4-pyrimidinediyl) diimino]bis-phenol, pyrimidine derivatives, and any combination and/or combinations thereof.

A sixth embodiment of the present disclosure includes any one of the first to the fifth embodiments, wherein the spleen tyrosine kinase inhibitor is imatinib.

A seventh embodiment of the present disclosure includes any one of the first to the sixth embodiments, wherein the spleen tyrosine kinase inhibitor is imatinib mesylate.

An eighth embodiment of the present disclosure includes a method of inhibiting the release of erythrocyte-derived microparticles into the blood of a patient, comprising the steps of: providing a spleen tyrosine kinase inhibitor to erythrocytes of a patient; and disrupting the binding of the spleen tyrosine kinase to a Band 3 docking protein.

A ninth embodiment of the present disclosure includes the eighth embodiment, wherein the spleen tyrosine kinase inhibitor is at least one inhibitor selected from the group consisting of: spleen tyrosine kinase inhibitor II, spleen tyrosine kinase inhibitor IV, imatinib, imatinib mesylate, NVP-QAB205, purine-2-benzamine derivatives, 1,6-naphthyridine derivatives, BAY 61-3606, piceatannol, 3,4-dimethyl-10-(3-aminopropyl)-9-acridone oxalate), 3,4-dimethyl-10-(3-aminopropyl)-9-acridone oxalate, substituted azaindoles, Fostamatinib disodium, tamatinib, oxindoles, 3,3'-[(5-Fluoro-2,4-pyrimidinediyl)diimino]bis-phenol, pyrimidine derivatives, and any combination and/or combinations thereof.

A tenth embodiment of the present disclosure includes any one of the eighth and the ninth embodiments, wherein the spleen tyrosine kinase inhibitor is imatinib.

An eleventh embodiment of the present disclosure includes any one of the eighth to the ninth embodiments, wherein the spleen tyrosine kinase inhibitor is imatinib mesylate.

A twelfth embodiment of the present disclosure includes a method of inhibiting intravascular hemolysis, comprising the steps of: administering to a patient at risk of having intravascular hemolysis a therapeutically effective dose of a tyrosine kinase inhibitor.

A thirteenth embodiment of the present disclosure includes the twelfth embodiment, wherein the therapeutically effective dose of the tyrosine kinase inhibitor is in the ranges selected from the group consisting of: about 100 mg/day to about 2000 mg/day, about 100 to about 2000 mg/day, about 100 to about 1800 mg/day, about 100 to about 1600 mg/day, about 100 to about 1400 mg/day, about 100 to about 1200 mg/day, about 100 to about 1000 mg/day, about 100 to about 800 mg/day, about 100 to about 600 mg/day, about 100 to about 400 mg/day, from about 100 to about 200 mg/day, and wherein the dose of the tyrosine kinase inhibitor is administered to the patient at least once per day.

A fourteenth embodiment of the present disclosure includes any one of the twelfth and the thirteenth embodiments, wherein the therapeutically effective dose of the tyrosine kinase inhibitor is on the order of between about 200 mg/day and about 500 mg/day and the dose of the tyrosine kinase inhibitor is administered to the patient at least once per day.

A fifteenth embodiment of the present disclosure includes any one of the twelfth to the fourteenth embodiments, wherein the tyrosine kinase inhibitor is a spleen tyrosine kinase inhibitor.

A sixteenth embodiment of the present disclosure includes any one of the twelfth to the fifteenth embodiments, wherein the spleen tyrosine kinase inhibitor is at least one inhibitor selected from the group consisting of: spleen tyrosine kinase inhibitor II, spleen tyrosine kinase inhibitor IV, imatinib, imatinib mesylate, NVP-QAB205, purine-2-benzamine derivatives, 1,6-naphthyridine derivatives, BAY 61-3606, piceatannol, 3,4-dimethyl-10-(3-aminopropyl)-9-acridone oxalate), 3,4-dimethyl-10-(3-aminopropyl)-9-acridone oxalate, substituted azaindoles, Fostamatinib disodium, tamatinib, oxindoles, 3,3'-[(5-Fluoro-2,4-pyrimidinediyl)diimino]bis-phenol, pyrimidine derivatives, and any combination and/or combinations thereof.

A seventeenth embodiment of the present disclosure includes any one of the twelfth to the sixteenth embodiments, wherein the spleen tyrosine kinase inhibitor is imatinib.

An eighteenth embodiment of the present disclosure includes any one of the twelfth to the seventeenth embodiments, wherein the spleen tyrosine kinase inhibitor is imatinib mesylate.

A nineteenth embodiment of the present disclosure includes any one of the twelfth to the eighteenth embodiments, wherein the intravascular hemolysis contributes to at least one symptom of sickle cell disease.

A twentieth embodiment of the present disclosure includes any one of the twelfth to the nineteenth embodiments, wherein the intravascular hemolysis contributes to at least one symptom of thalassemia.

In some embodiments a method is presented to prevent thrombosis in blood vessels of patients with a hemolytic disease comprising administration to a patient with at least one hemolytic disease a therapeutically effective amount of a tyrosine kinase inhibitor. In some embodiments the method includes repeatedly administering the tyrosine kinase inhibitor. In some embodiments the method includes a SYK inhibitor. In one aspect, the disclosure provides methods of inhibiting SYK signaling in vivo or in vitro, comprising administration of an effective amount of a SYK inhibitor. In other aspects, the method includes imatinib mesylate, one or more analogs of imatinib, or different salts or other forms of imatinib. In other aspects, the tyrosine kinase inhibitor is GLEEVEC. In some embodiments the hemolytic disease is sickle cell disease. In other aspects, the hemolytic disease is a thalassemia.

In some embodiments the methods include preventing destabilization of the erythrocyte membrane in a patient with at least one hemolytic disease comprising administration of a therapeutically effective amount of tyrosine kinase inhibitor to a patient with at least one hemolytic disease. In certain aspects, the administration of a therapeutically effective amount is given repeatedly. In certain aspects the tyrosine kinase inhibitor is a spleen tyrosine kinase inhibitor. In certain aspects the spleen tyrosine kinase inhibitor is GLEEVEC.

In some embodiments the methods include preventing erythrocyte hemolysis in a patient with at least one hemolytic disease comprising administration of a therapeutically effective amount of tyrosine kinase inhibitor to a patient with at least one hemolytic disease. In some aspects, wherein the administration of tyrosine kinase inhibitor is given repeatedly. In certain aspects, the tyrosine kinase inhibitor is a spleen tyrosine kinase inhibitor. In certain aspects, the hemolytic disease is sickle cell disease. In some aspects, the hemolytic disease is thalassemia.

In some embodiments a method is provided to prevent the migration of Band 3 along the membrane of an erythrocyte comprising introducing a spleen tyrosine kinase inhibitor to an erythrocyte. In some aspects, the introduction occurs through the membrane and into the cytoplasm of the erythrocyte. In some aspects, the spleen tyrosine kinase inhibitor is imatinib mesylate, one or more analogs of imatinib, or different salts or other forms of imatinib. In certain aspects, the spleen tyrosine kinase inhibitor is GLEEVEC.

In some embodiments a method is provided of preventing the exposure of phosphatidylserine residues on the outer surface of a microparticle or vesicle derived from fragments of a disrupted erythrocyte cell membrane comprising introduction of a spleen tyrosine kinase inhibitor to intact red blood cells. In certain aspects, the introduction occurs through the membrane of the red blood cells. In some aspects, the vesicle is a vesicle expelled from a destabilized erythrocyte. In some aspects, the prevention of exposure of phosphatidylserine residues prevents thrombosis.

In some embodiments, a method is presented of preventing vaso-occlusive crises comprising administering to a patient in need thereof a therapeutically effective amount of a tyrosine kinase inhibitor. In some aspects, the tyrosine kinase inhibitor inhibits the tyrosine phosphorylation of erythrocyte membrane protein termed Band 3. In some aspects, the tyrosine kinase that is inhibited is erythrocyte p72SYK.

In yet another embodiment in any of the above methods, the SYK inhibitor is selected from the group consisting of SYK inhibitor II, SYK inhibitor IV, imatinib mesylate and combinations thereof.

In one embodiment, the disclosure relates to a method for treating a hemolytic disease comprising: (a) identifying a patient in need of treatment from a hemolytic disease; and (b) administering to said patient a therapeutically effective amount of a SYK inhibitor to treat the hemolytic disease. The method further comprising identifying a patient prior to showing any symptoms. In another embodiment the patient is given a prophylactic treatment. In certain aspects the hemolytic disease is sickle cell disease. In other aspects, the disease is alpha or beta thalassemia. In other aspects, the disease is diabetes mellitus. In other aspects, the disease is caused by red cell oxidative stress.

The disclosure provides details on a new method of alleviating the chronic pain of sickle cell disease and preventing vaso-occlusive crises comprising the administration to a patient in need thereof a therapeutically effective amount of a tyrosine kinase inhibitor. In some embodiments the method includes repeatedly administering the tyrosine kinase inhibitor. In some embodiments the method includes a spleen tyrosine kinase (SYK) inhibitor. In one aspect, the disclosure provides a method of interfering with the phosphorylation of tyrosine residues 8 and 21 on the erythrocyte membrane protein known as Band 3. In other aspects, the method includes imatinib mesylate, one or more analogs of imatinib, or different salts or other forms of imatinib. In other aspects, the tyrosine kinase inhibitor is GLEEVEC.

In other aspects, a method is presented to interfere with the phosphorylation of a protein Band 3 comprising introduction of a spleen tyrosine kinase inhibitor to an erythrocyte. In some embodiments, the method includes introducing a kinase inhibitor through the membrane and into the cytoplasm of the erythrocyte. In other aspects, the method includes imatinib mesylate, one or more analogs of imatinib, or different salts or other forms of imatinib. In other aspects, the tyrosine kinase inhibitor is GLEEVEC.

In some embodiments a method is presented to prevent thrombosis in blood vessels of patients with a hemolytic disease comprising administration to a patient with at least one hemolytic disease a therapeutically effective amount of a tyrosine kinase inhibitor. In some embodiments the method includes repeatedly administering the tyrosine kinase inhibitor. In some embodiments the method includes a SYK inhibitor. In one aspect, the disclosure provides methods of inhibiting SYK signaling in vivo or in vitro, comprising administration of an effective amount of a SYK inhibitor. In other aspects, the method includes imatinib mesylate, one or more analogs of imatinib, or different salts or other forms of imatinib. In other aspects, the tyrosine kinase inhibitor is GLEEVEC. In some embodiments the hemolytic disease is sickle cell disease. In other aspects, the hemolytic disease is a thalassemia.

In some embodiments the methods include preventing destabilization of the erythrocyte membrane in a patient with at least one hemolytic disease comprising administration of a therapeutically effective amount of tyrosine kinase inhibitor to a patient with at least one hemolytic disease. In certain aspects, the administration of a therapeutically effective amount is given repeatedly. In certain aspects the tyrosine kinase inhibitor is a spleen tyrosine kinase inhibitor. In certain aspects the spleen tyrosine kinase inhibitor is GLEEVEC.

In some embodiments the methods include preventing erythrocyte hemolysis in a patient with at least one hemolytic disease comprising administration of a therapeutically effective amount of tyrosine kinase inhibitor to a patient with at least one hemolytic disease. In some aspects, wherein the administration of tyrosine kinase inhibitor is given repeatedly. In certain aspects, the tyrosine kinase inhibitor is a spleen tyrosine kinase inhibitor. In certain aspects, the hemolytic disease is sickle cell disease. In some aspects, the hemolytic disease is thalassemia.

In some embodiments a method is provided to prevent the migration of Band 3 along the membrane of an erythrocyte comprising introducing a spleen tyrosine kinase inhibitor to an erythrocyte. In some aspects, the introduction occurs through the membrane and into the cytoplasm of the erythrocyte. In some aspects, the spleen tyrosine kinase inhibitor is imatinib mesylate, one or more analogs of imatinib, or different salts or other forms of imatinib. In certain aspects, the spleen tyrosine kinase inhibitor is GLEEVEC.

In some embodiments a method is provided of preventing the exposure of phosphatidylserine residues on the outer surface of a microparticle or vesicle derived from fragments of a disrupted erythrocyte cell membrane comprising introduction of a spleen tyrosine kinase inhibitor to intact red blood cells. In certain aspects, the introduction occurs through the membrane of the red blood cells. In some aspects, the vesicle is a vesicle expelled from a destabilized erythrocyte. In some aspects, the prevention of exposure of phosphatidylserine residues prevents thrombosis.

In some embodiments, a method is presented of preventing vaso-occlusive crises comprising administering to a patient in need thereof a therapeutically effective amount of a tyrosine kinase inhibitor. In some aspects, the tyrosine kinase inhibitor inhibits the tyrosine phosphorylation of erythrocyte membrane protein termed Band 3. In some aspects, the tyrosine kinase that is inhibited is erythrocyte p72SYK.

In yet another embodiment in any of the above methods, the SYK inhibitor is selected from the group consisting of SYK inhibitor II, SYK inhibitor IV, imatinib mesylate and combinations thereof.

In one embodiment, the disclosure relates to a method for treating a hemolytic disease comprising: (a) identifying a patient in need of treatment from a hemolytic disease; and (b) administering to said patient a therapeutically effective amount of a SYK inhibitor to treat the hemolytic disease. The method further comprising identifying a patient prior to showing any symptoms. In another embodiment the patient is given a prophylactic treatment. In certain aspects the hemolytic disease is sickle cell disease. In other aspects, the disease is alpha or beta thalassemia. In other aspects, the disease is diabetes mellitus. In other aspects, the disease is caused by red cell oxidative stress.

In one embodiment, the disclosure relates to a method of treating at least one hemolytic disease comprising administering an effective amount of a SYK inhibitor to a subject in need of treatment. In one embodiment, more than one SYK inhibitor can be used. In another embodiment, two or more SYK inhibitors can be used, wherein the inhibitors are administered sequentially. In another embodiment, two or more SYK inhibitors can be used, wherein the inhibitors are administered concurrently or simultaneously.

Any SYK inhibitor or combination of SYK inhibitors that achieves the desired result may be used in the compositions and methods disclosed herein. One or more than one SYK inhibitor can be used.

In one embodiment, any number and any combination of SYK inhibitors can be used, including but not limited to 1, 2, 3, 4, 5, 6, 7, 8, 9, 10, 11-15, 16-20, and 21-25, 26-35, 36-50, 51-100, 101-150, 151-200, and greater than 200 SYK inhibitors. One or more than one mechanism of inhibition may be used including but not limited to small molecule inhibitors, siRNA, mRNA, RNA interference, and small interfering RNA.

In another embodiment, any dosage or concentration of SYK inhibitor that achieves the desired result may be used including but not limited to from 100 to about 2000 mg/day, from about 100 to about 1800 mg/day, from about 100 to about 1600 mg/day, from about 100 to about 1400 mg/day, from about 100 to about 1200 mg/day, from about 100 to about 1000 mg/day, from about 100 to about 800 mg/day, from about 100 to about 600 mg/day, from about 100 to about 400 mg/day, and from about 100 to about 200 mg/day.

In another embodiment, any dosage or concentration of SYK inhibitor that achieves the desired result may be used including but not limited to from about 200 to about 2000 mg/day, from about 200 to about 1800 mg/day, from about 200 to about 1600 mg/day, from about 200 to about 1400 mg/day, from about 200 to about 1200 mg/day, from about 200 to about 1000 mg/day, and from about 200 to about 800 mg/day. Yet another embodiments, any dosage or concentration of SYK inhibitor that achieves the desired result may be used including but not limited to, about 200, 300, 400, 500, 600, 700, 800, 900, 1000, 1100, 1200, 1300, 1400, 1500, 1600, 1700, 1800, 1900, or 2000 mg/day.

In one embodiment, the SYK inhibitor can inhibit or reduce the activity of SYK by any amount including but not limited to 1-5%, 5-10%, 10-20%, 20-30%, 30-40%, 40-50%, 50-60%, 60-70%, 70-80%, 80-90%, 90-95%, and 95-99%, 99-200%, 200-300%, 300-400%, 400-500% and greater than 500% as compared to the normal activity of SYK without the inhibitor.

In one embodiment, the SYK inhibitor can inhibit or reduce the activity of SYK from about 5% to about 20%, from about 5% to about 30%, from about 5% to about 40%, from about 5% to about 50%, from about 5% to about 60%, from about 5% to about 70%, from about 5% to about 80%, from about 5% to about 90%, and from about 5% to about 95% as compared to the normal activity of SYK without the inhibitor.

In one embodiment, imatinib mesylate is administered with one or more SYK inhibitors. In still another embodiment, imatinib mesylate is administered with one or more drugs used to treat pain.

In yet another embodiment, imatinib mesylate is administered from about 100 to about 1200 mg/day. In another embodiment, imatinib mesylate is administered from about 400 to about 1200 mg/day. In another embodiment, imatinib mesylate is administered from about 400 to about 1000 mg/day. In another embodiment, imatinib mesylate is administered from about 400 to about 800 mg/day. In another embodiment, imatinib mesylate is administered from about 400 to about 600 mg/day.

It should be recognized that the SYK inhibitors disclosed herein may be present and optionally administered in the form of salts, hydrates and prodrugs that are converted in vivo into SYK inhibitors. For example, it is within the scope of the disclosure to convert the SYK inhibitors of the disclosure into and use them in the form of their pharmaceutically acceptable salts derived from various organic and inorganic acids and bases in accordance with procedures well known in the art.

BRIEF DESCRIPTION OF THE FIGURES

FIG. 1A shows the microparticle concentration in plasma from a healthy, normal human control;

FIG. 1B shows the microparticle concentration in plasma from a non-splenectomized thalassemia patient; and FIG. 1C shows the microparticle concentration from a splenectomized thalassemia patient.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

As used herein, the term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

As used herein, "cell" or "cells," unless specifically limited to the contrary, includes any somatic cell, embryonic stem (ES) cell, adult stem cell, an organ specific stem cell, nuclear transfer (NT) units, and stem-like cells. The cell or cells can be obtained from any organ or tissue. The cell or cells can be human or other animal. For example, a cell can be mouse, guinea pig, rat, cattle, horses, pigs, sheep, goats, etc. A cell also can be from non-human primates.

Unless specifically or implicitly stated otherwise the term 'about' as used herein means plus or minus 10 percent. For example, 'about 1.0' encompasses the range of 0.9 to 1.1.

A therapeutically effective amount is an amount of a biologically active compound that has a single or cumulative beneficial effect on the health or well being of a patient.

The terms "inhibit", "inhibiting", "inhibition" and grammatical variations thereof as used herein refer to reduction including but not limited to completely elimination an event or an a activity, for an example a molecular or physiological process or the activity of a catalyst including, for example, an enzyme or a plurality of enzymes.

In another aspect, to "inhibit" is to destroy, prevent, control, decrease, slow or otherwise interfere with the growth or survival of a pathogen or pathological event by at least about 1-fold or more, for example, about 1.5-fold to about 100-fold, or any value in between for example by at least about 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95-fold when compared to the growth or survival of the pathogen, or progress of the pathology, in an untreated control.

As used herein, "small molecule" refers to a non-peptidic, non-oligomeric organic compound either synthesized in the laboratory or found in nature. Small molecules, as used herein, can refer to compounds that are "natural product-like," however, the term "small molecule" is not limited to "natural product-like" compounds. Rather, a small molecule is typically characterized in that it possesses one or more of the following characteristics including having at least one carbon-carbon bond, having at least one stereocenters, having at least one functional group, when there is more than one functional group they may be the same or different, having a molecular weight of less than 1500, although this characterization is not intended to be limiting for the purposes of the disclosure.

As used herein, "mammal" includes, without limitation, humans and other primates, domestic animals (e.g., dogs or cats), farm animals (cows, horses, or pigs), rabbits, mice, and laboratory animals.

As used herein "hemolytic disease" refers to a disease of the blood in which the contents of red blood cells (erythrocytes), including hemoglobin, heme and iron, escape from the cell and become part of the circulating blood serum. Heme and unchelated iron are toxic to the liver, the spleen and other organs. Since either full or partial damage to red bloods cell results in a reduction in the total number of such cells in circulation, hemolytic diseases are also often called hemolytic anemias.

As used herein, "patient" refers to human and non-human animals, especially mammals. Examples of patients include, but are not limited to, humans, non-human primates, cows, dogs, cats, goats, sheep, pigs and rabbits.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount," "therapeutically effective amount," or "therapeutically effective dose" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount may vary depending on the compound, the disorder or condition and its severity.

The terms "prevent," "preventing," "prevention" and grammatical variations thereof as used herein, refers to a method of partially or completely delaying or precluding the onset or recurrence of a disorder or condition and/or one or more of its attendant symptoms or barring a subject from acquiring or reacquiring a disorder or condition or reducing a subject's risk of acquiring or re-acquiring a disorder or condition or one or more of its attendant symptoms.

The term "subject" is defined herein to include animals such as mammals, including, but not limited to, primates (e.g., humans), cows, sheep, goats, horses, dogs, cats, rabbits, rats, mice and the like. In one embodiment, the subject is a human.

The term "SYK inhibitor" refers to any agent that inhibits the catalytic activity of the protein known as Spleen Tyrosine Kinase. In the abbreviation the letter "Y" is the single letter symbol designating the amino acid tyrosine. As used herein, SYK inhibitor includes small molecules, antibodies, and peptides.

The terms "treat," "treating," "treatment" and grammatical variations thereof as used herein, includes partially or completely delaying, alleviating, mitigating or reducing the intensity of one or more attendant symptoms of a disorder or condition and/or alleviating, mitigating or impeding one or more causes of a disorder or condition. Treatments according to the disclosure may be applied preventively, prophylactically, palliatively or remedially.

Band 3 is the predominant trans-membrane protein commonly found in erythrocyte cells. Characteristics of Band 3 are as follows: Band 3 catalyzes the exchange of anions (primarily bicarbonate $HCO_3^-$ for chloride $Cl^-$) across the erythrocyte membrane. Band 3 anchors the spectrin/actin cytoskeleton to the lipid bilayer, and organizes and regulates a complex of glycolytic enzymes. Band 3 participates in control of erythrocyte lifespan. It nucleates several important membrane-spanning proteins. Band 3 serves as a docking site for multiple peripheral membrane proteins, including protein 4.1, protein 4.2, and several kinases and phosphatases. In response to physiologic stimuli (such as hypertonic conditions or oxidative stress) and in severe hematologic disorders such as thalassemia, sickle cell anemia, and glucose-6-phosphate dehydrogenase deficiency, phosphorylation of Band 3 on tyrosine residues can increase by several orders of magnitude. Band 3 is also a prominent substrate of Ser/Thr kinases and is the major substrate of the cell's protein tyrosine kinases. Importantly, mutations in Band 3 are frequently associated with various hemolytic diseases.

Band 3 tyrosine phosphorylation significantly impacts erythrocyte function in a number of fashions. Band 3 organizes a complex of glycolytic enzymes on the membrane and thereby controls the flux of glucose between the pentose phosphate pathway (PPP) and glycolysis. Syk phosphorylation of band 3 leads to displacement of these glycolytic enzymes from an inhibitory site on band 3, resulting in activation of glycolysis. This activation shifts the consumption of glucose from PPP to glycolysis, resulting in a decline in RBC reducing power and a concomitant increase in RBC ATP. Phosphorylation of Band 3 has also been shown to inhibit band 3 mediated anion transport.

Band 3 is prominently engaged in anchoring of the membrane cytoskeleton to the lipid bilayer. This Band 3 function is linked specifically to its association with adducin at the junctional complex and ankyrin at the ankyrin complex. Rupture of either of these two bridges yields an erythrocyte that spontaneously loses membrane surface through vesiculation/blebbing. Syk-mediated tyrosine phosphorylation of Band 3 has been demonstrated to lead to complete inhibition of ankyrin binding and the consequent dissociation of Band 3 from the cytoskeleton. When induced in freshly isolated erythrocytes in suspension, tyrosine phosphorylation of Band 3 surprisingly results in major changes in RBC morphology without loss of membrane surface area. However, when the same RBCs are even slightly mechanically agitated (e.g. rocking the suspension), they immediately bleb membrane surface and vesiculate. Indeed, membrane vesiculation in vivo constitutes a common characteristic of erythrocyte pathologies (sickle cell disease, G6PDH deficiency, β-thalassemia) that are characterized by elevated Band 3 tyrosine phosphorylation. In these diseases, the released microparticles, as they are termed in the literature, are thought to promote thrombosis and its associated morbidities. Previously, the inventors have demonstrated that inhibition of p72Syk-mediated phosphorylation of Band 3 during the later stages of parasite maturation might block parasite egress from the infected red blood cells, leaving the infected cell filled with merozoites that are unable to release into the blood. See also U.S. Patent Publication No. 20140309233, disclosures of which are incorporated by reference in its entirety to the extent they are not inconsistent with the explicit teachings of this specification.

Syk kinase plays an essential role in lymphocyte development and activation of immune cells and is best characterized for its role in B cell receptor signaling and Fc receptor mediated release of mast cell granules. Although expressed ubiquitously in hematopoietic cells, Syk is also expressed in other tissues, such as breast epithelial cells and hepatocytes.

"Syk" or "Syk kinase" refers to the 72 kDa non-receptor (cytoplasmic) spleen protein tyrosine kinase expressed in B-cells and other hematopoetic cells. Syk kinase is characterized by two consensus Src-homology 2 (SH2) domains in tandem that bind to phosphorylated immunoreceptor tyrosine-based activation motifs ("ITAMs"), a "linker" domain and a catalytic domain (for a review, see Sada et al., 2001, J. Biochem. (Tokyo) 130:177-186 and also Turner et al., 2000, Immunology Today 21:148-154 and Wong et al., 2004, Expert Opin Investig Drugs 13(7):743-62).

Syk kinase is also critical for tyrosine phosphorylation of multiple proteins that regulate important pathways leading from immunoreceptors, such as $Ca^{2+}$ mobilization and mitogen-activated protein kinase (MAPK) cascades and degranulation. Syk kinase also plays a critical role in integrin signaling in neutrophils (see, e.g., Mocsai et al. 2002, Immunity 16:547-558).

Syk kinase includes kinases from any species of animal, including but not limited to, *Homo sapiens*, simian, bovine, porcine, rodent, etc., recognized as belonging to the Syk family. Specifically included are isoforms, splice variants, allelic variants, mutants, both naturally occurring and man-made. The amino acid sequences of such Syk kinases are available from GENBANK. Specific examples of mRNAs encoding different isoforms of human Syk kinase are available at GENBANK accession no. gi|21361552|ref|NM.sub.--003177.2, gi|496899|emb|Z29630.1|HSSYKPTK[496899] and gi|15030258|gb|BC011399.1|BC011399[15030258], which are incorporated herein by reference.

The major erythrocyte membrane protein, Band 3 (AE1, SLC4A1, anion transporter) forms the predominant bridge connecting the red cell membrane to its spectrin/actin cytoskeleton via an association with ankyrin. The tyrosine phosphorylation of Band 3 has been demonstrated to cause dissociation of ankyrin, leading to rupture of this membrane-to-cytoskeleton bridge and the consequent membrane destabilization, vesiculation and hemolysis.

Figure 2:
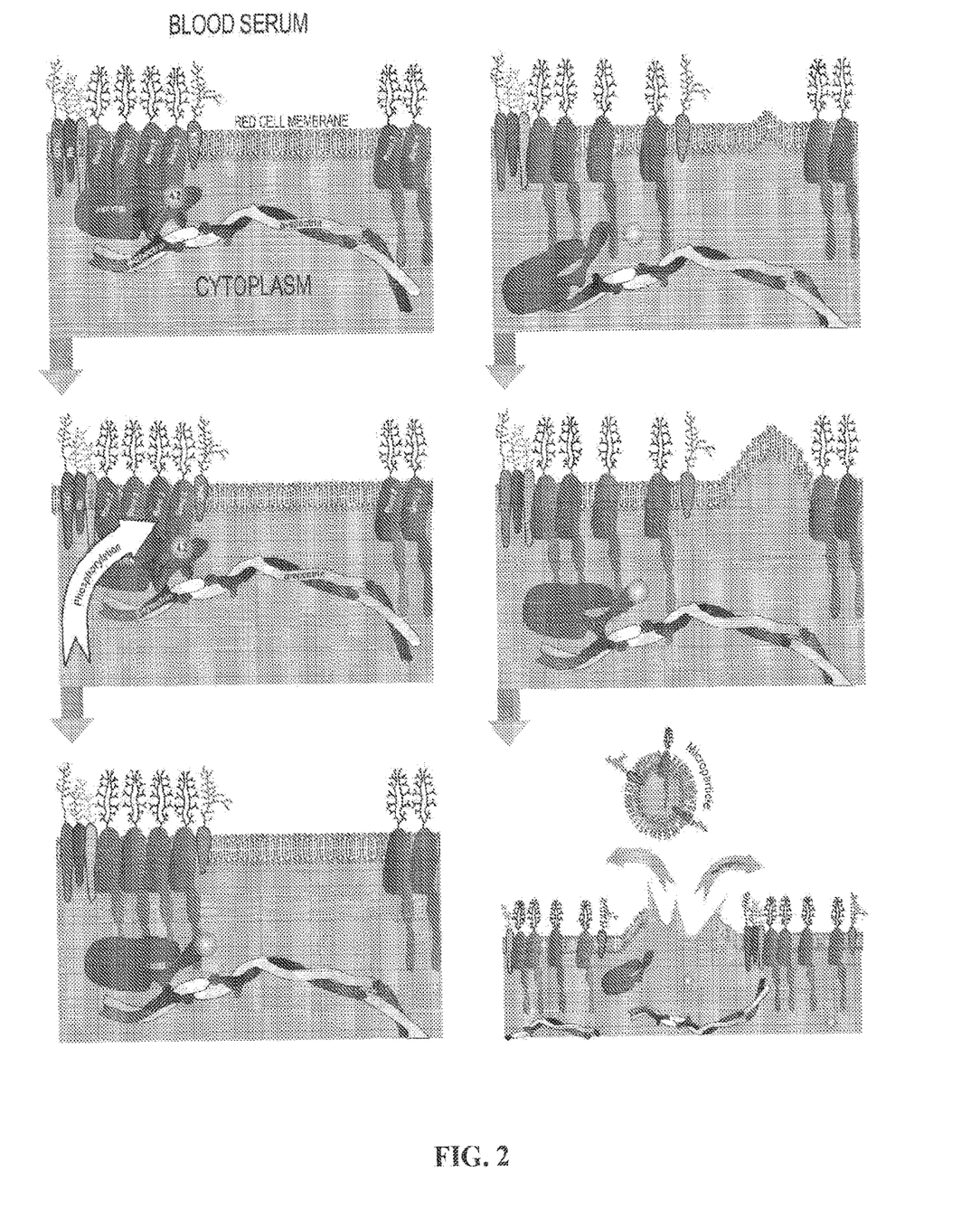
FIG. 2 is a cartoon schematic with six panels showing the instability of the red cell membrane when Band 3 is phosphorylated and disengages ankyrin and junctional complexes that connect the lipid bilayer to the spectrin cytoskeleton resulting in microparticle release from the red blood cell.

Referring now to FIG. 2, Band 3 represents a major component of the ankyrin and junctional complexes that connect the lipid bilayer to the spectrin cytoskeleton. Phosphorylation of Band 3 is associated with multiple kinases, but SYK is felt to play the most prominent role, because it has been reported to phosphorylate tyrosine residues 8 and 21 of Band 3, which in turn generates a binding site for other protein tyrosine kinases. When SYK docks to tyrosine residues in Band 3, the affinity of Band 3 for ankyrin decreases dramatically and it disengages the membrane from its cytoskeleton. This is followed by an increase in both lateral mobility of Band 3 within the membrane bilayer, the vesiculation of the red blood cells, release of microparticles exposing phosphatidylserine on their outer surface, release of free heme and hemoglobin and the loss of plasma membrane. Further understanding and explanation of the exposure of phosphatidylserine and microparticles can be found in Camus S. M., et al., *Circulating Cell Membrane Microparticles Transfer Heme to Endothelial Cells and Trigger Vaso-Occlusions in Sickle Cell Disease*, BLOOD, 2015 Mar. 31, DOI 10.1182/blood-2014-07-589283, disclosures of which are incorporated by reference in its entirety to the extent they are not inconsistent with the explicit teachings of this specification.

Figure 1A:
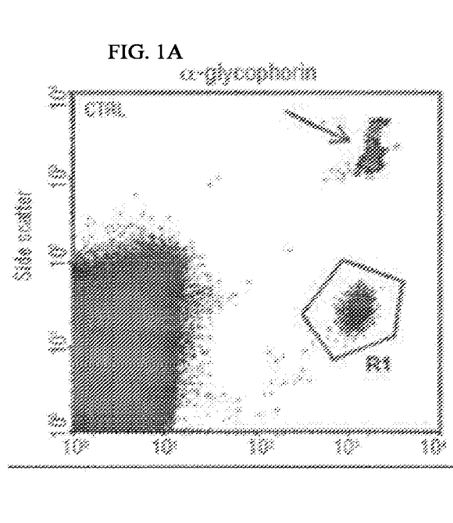
FIG. 1A-1C are graphs from flow cytometry analysis measuring microparticles in plasma designated as R1 and an arrow identifying a group of fluorescent CytoCount beads which provide a reference density for calculating the density of glycophorin-A microparticles.
Figure 1B:
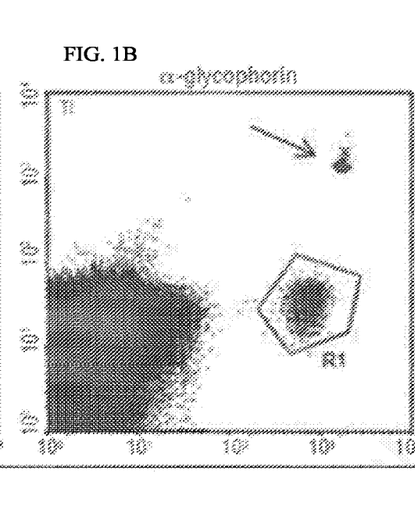
Figure 1C:
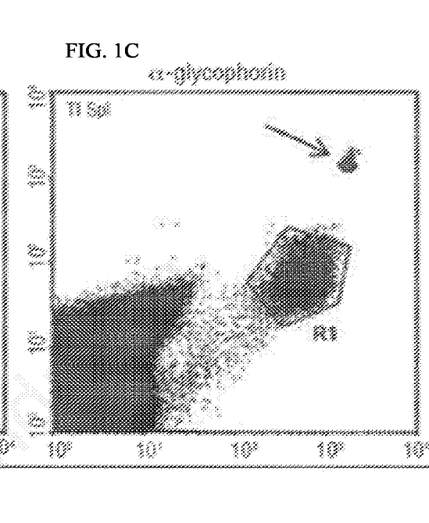

Referring now to FIGS. 1A-1C, methods and materials are adapted from Ferru E, et al., *Thalassemic erythrocytes release microparticles loaded with hemichromes by redox activation of p72Syk kinase*, Haematologica 2014, 3: 570-578, disclosures of which are incorporated by reference in its entirety to the extent they are not inconsistent with the explicit teachings of this specification.

Red Blood Cell Membrane Preparation. Standard hypotonic membranes were prepared, as previously described, and stored frozen at −80° C. until use. Membrane protein content was quantified using the DC Protein assay (Biorad, Hercules, Calif., USA).

Analysis of Microparticles. The MP in plasma were analyzed by flow cytometry using a modification of a previously described method: 25 μL of plasma diluted 1:1 with PBS-glucose 5 mM were analyzed using anti-CD41 (BD, Franklin Lakes, N.J., USA) and anti-glycophorin-A (Dako, Denmark), both diluted 1:10.

Microparticle Isolation. To induce MP release in vitro, RBC from each volunteer and phenylhydrazine-treated RBC in PBS (30% hematocrit) were incubated as previously described.

Electrophoresis and Immunoblotting. Membrane and MP proteins were solubilized in Laemmli buffer under reducing [2% (w/v) dithiothreitol] or non-reducing conditions at a volume ratio of 1:1. Sodium dodecylsulfate polyacrylamide gel electrophoresis (SDS-PAGE) was conducted. Western blot analysis was performed using anti-phosphotyrosine (Santa Cruz, Calif., USA), anti-band 3 and anti-IgG antibodies.

Referring now to FIGS. 1A-1C, splenectomies in these patients can trigger a rise in MP and severe thrombosis. Band 3 in such patients has been shown to be hyper phosphorylated. The use of SYK inhibitors in these cases will significantly decrease Band 3 tyrosine phosphorylation, the number of MP in circulation, and the amount of intravascular hemolysis. Because both MP and intravascular hemolysis have been associated with the onset of VOC, therapies that block Band 3 tyrosine phosphorylation will stabilize the red blood cell membrane and prevent the release of materials which can initiate thrombosis and inflammation on the lining (endothelium) of blood vessels and therefore inhibit or prevent VOC as well as the daily pain associated with multiple blockages of tiny capillaries and venules. Further understanding and explanation of microparticle differences between normal and thalassemia patients can be found in Ferru E, et al., *Thalassemic erythrocytes release microparticles loaded with hemichromes by redox activation of p72Syk kinase*, Haematologica 2014, 3: 570-578, disclosures of which are incorporated by reference in its entirety to the extent they are not inconsistent with the explicit teachings of this specification.

Examples of Syk kinase inhibitors include, but are not limited to, Syk kinase inhibitor II, Syk kinase inhibitor IV, imatinib, and imatinib mesylate.

As used herein, Syk kinase inhibitor II possesses the following structure:

In another embodiment, Syk kinase inhibitor II is designated chemically as 2-(2-Aminoethylamino)-4-(3-trifluoromethylanilino)-pyrimidine-5-carboxamide.

In yet another embodiment, Syk kinase inhibitor II is administered from about 200 to about 1200 mg/day. In another embodiment, Syk kinase inhibitor II is administered from about 400 to about 1200 mg/day or from about 400 to about 1000 mg/day or from about 400 to about 800 mg/day or from about 400 to about 600 mg/day. In one embodiment, Syk kinase inhibitor II is administered at about 800 mg/day.

As used herein, Syk kinase inhibitor IV possesses the following structure:

In yet another embodiment, Syk kinase inhibitor IV is administered from about 200 to about 1200 mg/day. In another embodiment, Syk kinase inhibitor IV is administered from about 400 to about 1200 mg/day or from about 400 to about 1000 mg/day or from about 400 to about 800 mg/day or from about 400 to about 600 mg/day. In one embodiment, Syk kinase inhibitor IV is administered at about 800 mg/day.

In one embodiment, the Syk kinase inhibitor is imatinib. Imatinib is designated chemically as 4-[(4-Methyl-1-piperazinyl)methyl]-N-[4-methyl-3-[[4-(3-pyridinyl)-2-pyrimidinyl]amino]-phenyl]benzamide and its structural formula is:

In one embodiment, the Syk kinase inhibitor is imatinib mesylate (GLEEVEC). Imatinib mesylate is designated chemically as 4-[(4-Methyl-1-piperazinyl)methyl]-N-[4-methyl-3-[[4-(3-pyridinyl)-2-pyrimidinyl]amino]-phenyl] benzamide methanesulfonate and its structural formula is:

Examples of Syk kinase inhibitors include, without limitation, NVP-QAB205; purine-2-benzamine derivatives such as those described in U.S. Pat. No. 6,589,950, hereby incorporated by reference herein; pyrimidine-5-carboxamide derivatives such as those described in PCT Publication No. WO 99/31073, hereby incorporated by reference herein; 1,6-naphthyridine derivatives such as those described in U.S. Patent Publication No. 2003/0229090, hereby incorporated by reference herein; BAY 61-3606; piceatannol; 3,4-dimethyl-10-(3-aminopropyl)-9-acridone oxalate); and combinations thereof.

Additional examples of Syk kinase inhibitors include, without limitation, compounds and derivatives disclosed in U.S. Patent Application Publication No. 20120130073; compounds and derivatives disclosed in U.S. Patent Application Publication No. 20100316649; compounds and derivatives disclosed in U.S. Pat. Nos. 8,057,815; 8,258,144; 8,227,455; 8,138,339; 8,063,058; 8,012,959; 7,842,712; 7,803,801; 7,705,004; 7,678,911; 7,547,794; 7,501,410; 7,449,456; 7,446,199; 7,321,041; 7,304,071; 7,276,502; 7,262,200; 7,173,015; 6,911,443; and 6,797,706; all of which are hereby incorporated by reference in their entirety.

ER-27319 (3,4-dimethyl-10-(3-aminopropyl)-9-acridone oxalate) can be used to inhibit Syk. Various concentrations of piceatannol (3,4,3'5'-tetrahydroxy-trans-stilbene) can also be used as a Syk kinase inhibitor, and possesses the following structure:

In addition to the inhibitors mentioned above, WO 0109134 discloses purine derivatives as inhibitors of SYK kinase. WO 0147922 describes substituted azaindoles useful in the treatment of disease states capable of being modulated by the inhibition of protein kinases, in particular SYK kinase. WO 9818782 describes inhibitors of ZAP70 that are also reported to inhibit SYK.

In one embodiment, R406 and derivatives thereof can be used to treat intravascular hemolysis, and possesses the following structure:

In another embodiment, R788, Fostamatinib disodium, (Rigel Pharmaceuticals) and derivatives thereof can be used to treat intravascular hemolysis, and possesses the following structure:

Fostamatinib is an experimental drug candidate for the treatment of a variety of diseases. It is in Phase III clinical trials for rheumatoid arthritis and Phase II trials for autoimmune thrombocytopenia and lymphoma. The oral drug is used as its disodium salt and it is a prodrug of the active compound tamatinib (R-406), which is an inhibitor of the enzyme spleen tyrosine kinase (Syk).

In one embodiment, compounds useful for treating intravascular hemolysis, and possesses the following structure:

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy; $R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from hydrogen, alkyl, substituted alkyl, alkenyl, substituted alkenyl, alkynyl, substituted alkynyl, acyl, acylamino, acyloxy, cycloalkyl, substituted cycloalkyl, cycloalkenyl, substituted cycloalkenyl, aralkyl, heteroaralkyl, aryl, substituted aryl, heteroaryl, substituted heteroaryl, heterocyclyl, and substituted heterocyclyl; or a salt or stereoisomer thereof.

In yet another embodiment, compounds useful for treating intravascular hemolysis, and possesses the following structure:

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy; $R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present:

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^4$ is selected from hydrogen, alkyl, substituted alkyl, amino, or —$NR^5R^6$;
$R^5$ is selected from hydrogen, alkyl, and substituted alkyl; and
$R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy, or a salt or stereoisomer thereof.

In another embodiment, oxindoles, including but not limited to compounds listed in Table 1, can be used to inhibit Syk activity.

Table 1. Comparison of the physiochemical properties and inhibitory activities of oxidoles in kinase and whole cell based assays.

Adopted from Lai et al, Biorganic and Medicinal Chemistry Letters, 12:3111-3114 (2003).

In another embodiment, compounds useful in the methods of the disclosure include but are not limited to:

TABLE 1

Comparison of the physiochemical properties and inhibitory activities of oxindoles in kinase and whole cell based assays.

Formula VI

| Compd | R1 | R2 | R3 | R4 | IC@ (nM) | IC@ (nM) | Solubility (mg L) | PSA |
|---|---|---|---|---|---|---|---|---|
| 1 | H | H | H | H | 128 | | | 121 |
| 2 | H | H | Me | H | 14 | 313 | | 108 |
| 3 | H | H | H | OMe | 28 | >10,000 | | 162 |
| 31 | H | H | Me | OMe | 5 | 1400 | <0.1 | 117 |
| 6 | Me | Me | Me | OMe | Inactive@ 80 µM | >10,000 | <0.1 | 94 |
| 7 | H | Me | Me | OMe | 20 | 110 | <0.1 | 105 |
| 8 | H | Ex | Me | OMe | 100 | | | 104 |
| 9 | H | @Bu | Me | OMe | 937 | | | 101 |
| 10 | H | p-MeOPhCH$_2$ | Me | OMe | 2@4 µM | | | 116 |
| 11 | H | CH$_2$COOH | Me | OMe | 658 | 1940 | 30 | 148 |
| 12 | H | CH$_2$CH$_2$C(—O)NH$_2$ | Me | OMe | 60 | >10,000 | 8 | 151 |
| 13 | H | CH$_2$C(—O)NH$_2$ | Me | OMe | 98 | >10,000 | 1 | 152 |
| 14 | H | H | CH$_2$COOH piperidine salt | OMe | 850 | | 70 | 163 |
| 15 | H | H | (CH$_2$)$_3$COOH | OMe | 14 | | | 163 |
| 16 | H | H | (CH$_2$)$_3$COOH | OMe | 11 | 20,700 | <0.1 | 163 |
| 17 | H | H | CH$_2$-m-C$_6$H$_4$-COOH | OMe | 27 | | | 149 |
| 18 | H | H | (CH$_2$)$_3$OH | OMe | 32 | >10,000 | <0.1 | 142 |
| 19 | H | H | (CH$_2$)$_3$CONH$_2$ | OMe | 12 | >10,000 | 5 | 164 |
| 20 | H | H | CH$_2$COO@Bu | OMe | 1000 | | | 140 |
| 21 | H | H | (CH$_2$)$_3$COOEt | OMe | 204 | | | 147 |
| 22 | H | H | (CH$_2$)$_3$COOEt | OMe | 678 | 6960 | <0.1 | 147 |
| 23 | H | H | (CH$_2$)@COOEt | OMe | 465 | 6300 | <0.1 | 147 |
| 24 | H | H | (CH$_2$)$_3$CO-moepholino | H | 133 | 5600 | <0.1 | 153 |
| 25 | H | H | (CH$_2$)$_3$CO-piperidine | H | 616 | >30,000 | 10 | 156 |

@indicates text missing or illegible when filed

The compounds above are described in Lai et al. (Biorganic and Medicinal Chemistry Letters 13:3111-3114, 2003), which is entitled "Potent Small Molecule Inhibitors of Spleen Tyrosine Kinase (Syk)", disclosures of which are incorporated by reference in its entirety to the extent they are not inconsistent with the explicit teachings of this specification.

In yet another embodiment, the Syk kinase inhibitor can have the chemical designation of: 3,3'-[(5-Fluoro-2,4-pyrimidinediyl)diimino]bis-phenol (R112).

In one embodiment, the Syk kinase inhibitor is a pyrimidine derivative. In one embodiment, the Syk kinase inhibitor is a N-phenyl-2-pyrimidine-amine derivative of Formula I:

Formula I

Wherein $R_1$ is 4-pyrazinyl, 1-methyl-1H-pyrrolyl, amino- or amino-lower alkyl-substituted phenyl wherein the amino group in each case is free, alkylated or acylated, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen; $R_2$ and $R_3$ are each independently of the other hydrogen or lower alkyl, one or two of the radicals $R_4$, $R_5$, $R_6$, $R_7$ and $R_8$ are each nitro, fluoro-substituted lower alkoxy or a radical of $N(R_9)$—C(=X)—(Y)$_n$—$R_{10}$.

Wherein $R_9$ is hydrogen or lower alkyl, X is oxo, thio, imino, N-lower alkyl-imino, hydroximino or O-lower alkyl-hydroximino, Y is oxygen or the group NH, N is 0 or 1 and $R_{10}$ is an aliphatic hydrocarbon radical having at least 5 carbon atoms, or an aromatic, aromatic-aliphatic, cycloaliphatic, cycloaliphatic-aliphatic, heterocyclic or hetero-cyclialiphatic radical, and the remaining radicals $R_4$, $R_5$, $R_6$, $R_7$ and $R_8$ are each independently of the others each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterifed hydroxy, free, alkylated or acylated amino or free or esterified carboxy, or a salt of such a compound having at least one salt-forming group.

In one embodiment, $R_{10}$ is a phenyl or naphthyl radical each of which is unsubstituted or substituted by cyano, trifluoromethyl, hydroxy, lower alkoxy, lower alkanoyloxy, halogen, amino, lower alkylamino, di-lower alkylamino, lower alkanoylamino, benzoylamino, carboxy, lower alkoxycarbonyl or by unsubstituted or substituted lower alkyl, or phenyl-lower alkyl wherein the phenyl radical is unsubstituted or substituted as indicated above, a cycloalkyl or cycloalkenyl radical having up to 30 carbon atoms, cycloalkyl-lower alkyl or cycloalkenyl-lower alkyl each having up to 30 carbon atoms in the cycloalkyl or cycloalkenyl moiety, a monocyclic radical having 5 or 6 ring members and 1-3 ring atoms selected from nitrogen, oxygen and sulfur, to which radical one or two benzene radicals may be fused, or lower alkyl substituted by such a monocyclic radical.

In one embodiment, the Syk kinase inhibitor has the structural formula of:

See U.S. Patent Publication No. 20140309233, disclosures of which are incorporated by reference in its entirety to the extent they are not inconsistent with the explicit teachings of this specification.

When SYK inhibitors possess a free base form, the SYK inhibitors can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galcterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the disclosure.

When the SYK inhibitors possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the SYK inhibitors. Further base salts include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the disclosure.

Prodrug derivatives of SYK inhibitors can be prepared by modifying substituents of SYK inhibitors disclosed herein that are then converted to a different substituent. It is noted that in many instances, the prodrugs themselves also fall within the scope of the range of compounds according to the disclosure. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), Bioorganic and Medicinal Chemistry Letters, Vol. 4, p. 1985, the contents of which are incorporated by reference.

Some embodiments relate to RNA molecules that target Syk kinase mRNA. For example, the disclosure relates to RNA molecules from about 19, 20 or 21 to about 23 nucleotides in length that direct cleavage and/or degradation of Syk kinase mRNA.

In one embodiment, the disclosure relates to the use of siRNA molecules, double stranded RNA molecules typically comprising two 20-23 nucleotide (nt) strands. SiRNAs suitable for use in the disclosure can be produced using any of a variety of approaches. The siRNA can be prepared in vitro and then introduced directly into cells (for example, by transfection). Alternatively, intracellular expression can be effected by transfecting into cells constructs (e.g., DNA-based vectors or cassettes) that express siRNA within cells.

More specifically, siRNA suitable for use in the disclosure can be prepared, for example, via chemical synthesis, in vitro transcription, enzymatic digestion of a longer dsRNA using an RNase III enzyme such as Dicer or RNase III, expression in cells from an siRNA expression plasmid or viral vector, or expression in cells from a PCR-derived siRNA expression cassette. Detailed descriptions of these various approaches are readily available and can be found, for example, at http://www.ambion.com/techlib/tn/103/2.html, www.bdbiosciences.com, www.oligoengine.com, www.genetherapysystems.com, www.dharmacon.com, http://www.mpibpc.gwdg.de/abteilungen/100/105/sirna.html, and/or in the references cited therein (which references are also incorporated herein by reference). (See also Sui et al, Proc Natl Acad Sci USA 99: 5515-20 (2002), Brummelkamp et al, Science 296:550-3 (2002), Paul et al, Nature Biotechnology 20:505-8 (2002), Lee et al, Nature Biotechnology 20: 500-5 (2002), Castanotto et al, RNA 8: 1454-60 (2002) and US Appln. 20030108923.)

A "pharmaceutically acceptable salt", as used herein, is intended to encompass any small molecule according to the disclosure that is utilized in the form of a salt thereof, especially where the salt confers on the compound improved pharmacokinetic properties as compared to the free form of compound or a different salt form of the compound. A pharmaceutically acceptable salt, as used herein, includes salts present in vivo.

The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

In one embodiment of this disclosure, a SYK inhibitor can be modified with an anionic substituent that renders the inhibitor a substrate of Band 3, the transmembrane, anion transporter of the red cell membrane. Because Band 3 is more highly expressed in erythrocytes than any other cell type in the body (most cells express no Band 3 whereas erythrocytes express 1,200,000 copies/cell), an otherwise poorly cell permeable SYK inhibitor that can enter erythrocytes via Band 3 will constitute an erythrocyte-specific SYK inhibitor. Such an erythrocyte-selective SYK inhibitor should exhibit reduced toxicity to non-erythroid cells requiring SYK activity for normal biologic function (e.g. B cells, platelets, etc.).

A wide variety of compositions and administration methods may be used in conjunction with SYK inhibitors of the disclosure. Such compositions may include, in addition to the SYK inhibitors of the disclosure, conventional pharmaceutical excipients, and other conventional, pharmaceutically inactive agents. Additionally, the compositions may include active agents in addition to the SYK inhibitors of the disclosure. These additional active agents may include additional compounds according to the disclosure, and/or one or more other pharmaceutically active agents.

The pharmaceutical compositions can be included in a container, pack, or dispenser together with instructions for administration.

The compositions may be in gaseous, liquid, semi-liquid or solid form, formulated in a manner suitable for the route of administration to be used. For oral administration, capsules, tablets, solutions, suspensions and fast-melting films are typically used. For inhalation, an aerosol or a dispersed microparticulate powder are common. For parenteral administration, sterile reconstitution of a lyophilized powder, prepared as described herein, is typically used.

Compositions comprising SYK inhibitors of the disclosure may be administered or co-administered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the disclosure may also be administered or coadministered in slow release dosage forms. The SYK inhibitors of the disclosure may be administered intravenously on the first day of treatment, with oral administration on the second day and all consecutive days thereafter.

The SYK inhibitors and compositions comprising them may be administered or coadministered in any conventional dosage form. Co-administration in the context of this disclosure is intended to mean the administration of more than one therapeutic agent, one of which includes a small molecule, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfate; chelating agents, such as ethylenediaminetetraacetic acid (EDTA); buffers, such as acetates, citrates and phosphates; agents for the adjustment of tonicity such as sodium chloride or dextrose, and agents foradjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampoules, disposable syringes or single or multiple dose vials made of glass, plastic or other suitable material.

For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin or talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more SYK inhibitors, optionally 0.1-95%, and optionally 1-95%.

Examples of pharmaceutically acceptable carriers that may be included in tablets comprising compounds of the present disclosure include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

The SYK inhibitors of the disclosure can be administered alone or in combination with other therapies suitable for the disease or disorder being treated. Where separate dosage formulations are used, the SYK inhibitors and the other therapeutic agent can be administered at essentially the same time (concurrently) or at separately staggered times (sequentially). The pharmaceutical combination is understood to include all these regimens. Administration in these various ways are suitable for the present disclosure as long as the beneficial therapeutic effect of the small molecule and the other therapeutic agent are realized by the patient at substantially the same time. In an embodiment, such beneficial effect is achieved when the target blood level concentrations of each active drug are maintained at substantially the same time.

The dosage regimen utilizing SYK inhibitors of the disclosure can be selected in accordance with a variety of factors including type, species, age, weight, sex and the type of hemolytic disease being treated; the severity (i.e., stage) of the disease to be treated; the route of administration; the pharmacogenomic characteristics of individual patients, including the frequency of polymorphism for any gene coding for enzymes involved in the metabolism of the molecules inhibiting SYK (such as cytochrome p450 enzymes); the renal and hepatic proficiency of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

In one embodiment the SYK inhibitor is administered repeatedly. In one aspect the SYK inhibitor is administered once daily. In another aspect the SYK inhibitor is administered twice daily. The SYK inhibitor may be administered continuously or intermittently.

In addition, the administration can be continuous, i.e., every day, or intermittently. The terms "intermittent" or "intermittently" as used herein means stopping and starting at either regular or irregular intervals. For example, intermittent administration of a small molecule may be administration one to six days per week or it may mean administration in cycles (e.g., daily administration for two to eight consecutive weeks, then a rest period with no administration for up to one week) or it may mean administration on alternate days.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method of inhibiting Band 3 tyrosine phosphorylation in a patient having sickle cell disease, which method comprises the steps of:
   (a) identifying a patient having sickle cell disease and showing no symptoms of sickle cell disease,
   (b) measuring Band 3 tyrosine phosphorylation levels in a sample of blood taken from the patient to identify a patient with elevated Band 3 tyrosine phosphorylation, and
   (c) treating the patient with a dosage regimen of repeated administration of a therapeutically effective amount of at least one agent that reduces Band 3 tyrosine phosphorylation;
   wherein the at least one agent that reduces Band 3 tyrosine phosphorylation is selected from the group consisting of spleen tyrosine kinase inhibitor II, spleen tyrosine kinase inhibitor IV, imatinib, imatinib mesylate, and combinations thereof.

2. The method of claim 1, further comprising measuring a total amount of red blood cell-derived microparticles in the blood stream of the patient.

3. The method of claim 2, further comprising assessing the degree of inflammation in blood vessels of the patient.

4. The method of claim 2, further comprising assessing the degree of thrombosis in the patient.

5. The method of claim 2, further comprising adjusting the dosage regimen when the total amount of red blood cell-derived microparticles remains elevated compared to the initial amount of red blood cell-derived microparticles.

6. The method of claim 1, wherein the therapeutically effective amount of at least one agent that reduces Band 3 tyrosine phosphorylation is between about 200 mg/day and about 500 mg/day.

7. The method of claim 1, wherein the therapeutically effective amount of at least one agent that reduces Band 3 tyrosine phosphorylation is between about 400 mg/day to about 800 mg/day.

* * * * *

UNITED STATES PATENT AND TRADEMARK OFFICE
CERTIFICATE OF CORRECTION

| | |
|---|---|
| PATENT NO. | : 11,446,297 B2 |
| APPLICATION NO. | : 15/566590 |
| DATED | : September 20, 2022 |
| INVENTOR(S) | : Low et al. |

It is certified that error appears in the above-identified patent and that said Letters Patent is hereby corrected as shown below:

On the Title Page

In item (71), in "Applicants", in Column 1, Line 1, delete "Research," and insert --Research Foundation,-- therefor Signed and Sealed this
Twenty-seventh Day of June, 2023

Katherine Kelly Vidal
*Director of the United States Patent and Trademark Office*